United States Patent [19]

Davidson

[11] Patent Number: 4,544,509

[45] Date of Patent: Oct. 1, 1985

[54] ARYL COUPLING PROCESS

[75] Inventor: Robert I. Davidson, Baton Rouge, La.

[73] Assignee: Ethyl Corporation, Richmond, Va.

[21] Appl. No.: 523,161

[22] Filed: Aug. 15, 1983

[51] Int. Cl.$^4$ .................... C07C 121/66; C07C 69/616
[52] U.S. Cl. ............................ 260/465 G; 260/465 D; 260/465 F; 560/21; 560/59; 560/81
[58] Field of Search .......... 260/465 F, 465 G, 465 D; 560/21, 59, 81

[56] References Cited

U.S. PATENT DOCUMENTS 4,266,069  5/1981  Walker .................................. 560/20

FOREIGN PATENT DOCUMENTS 2065655  7/1981  United Kingdom .

Primary Examiner—Nicky Chan
Attorney, Agent, or Firm—Donald L. Johnson; John F. Sieberth; Patricia J. Hogan

[57] ABSTRACT

An arylamine is coupled with an aromatic compound in the presence of water, an inorganic nitrite, and an alkanoic acid containing 5–7 carbons. In a preferred embodiment of the invention, 2-(4-amino-3-fluorobenzene)propionitrile is coupled with benzene in the presence of water, sodium nitrite, and hexanoic acid to form a flurbiprofen intermediate.

14 Claims, No Drawings

ARYL COUPLING PROCESS

TECHNICAL FIELD

This invention relates to biaryl compounds and more particularly relates to an aryl coupling process for preparing them.

BACKGROUND

As disclosed in U.K. Pat. No. 2 065 655 A (Upjohn) and in U.S. Pat. No. 4,266,069 (Walker), it is known that certain flurbiprofen-type intermediates can be prepared by coupling aminohalobenzenes, such as 4-bromo-2-fluoroaniline, diethyl 2-(4-amino-3-fluorophenyl)-2-methylmalonate, etc., with benzene compounds. The coupling techniques taught by Upjohn and Walker include reaction of the arylamines and benzene compounds in the presence of water, an inorganic nitrite, and a strong acid—a process which, when applied to the coupling of a 2-(4-amino-3-fluorobenzene)propionitrile with benzene, has been found to result in low yields of biaryl compound.

Copending application Ser. Nos. 488,192 now U.S. Pat. No. 4,482,502 (Ramachandran) and 488,068 (Ramachandran I), both filed Apr. 25, 1983, teach that it has been found difficult to obtain high yields of biaryl compound when arylamines bearing one or more acid-sensitive ar-substituents, e.g., cyanoalkyl, carboxyalkyl, and alkylcarboxyalkyl groups, have been coupled with benzene compounds. As revealed by Ramachandran and Ramachandran I, this has presented problems when it has been desired to prepare flurbiprofen intermediates from aminohalobenzenes such as 2-(4-amino-3-fluorobenzene)propionitrile and alkyl 2-(4-amino-3-fluorobenzene)propionates; and they have solved these problems by using copper/strong acid catalyst systems and/or temperature control in aryl coupling processes utilizing alkyl nitrites.

Although it has been found that the processes of Ramachandran and Ramachandran I can be employed quite advantageously in the preparation of biaryl compounds from difficulty-coupled arylamines, as well as from arylamines that are more easily coupled, it would be desirable to find an alternative process which would not require the use of costly and hazardous alkyl nitrites.

Rosenberg et al., "Conversion of Arenediazonium Tetrafluoroborates into Unsymmetrical Biaryls Using Catalysts Other than Polyethers," *Tetrahedron Letters*, Vol. 21, pp. 4141–4144 (1980), teach that arenediazonium salts can be coupled with benzene in the presence of potassium acetate and various phase-transfer catalysts, including long-chain alkali metal carboxylates.

SUMMARY OR INVENTION

An object of this invention is to provide a novel aryl coupling process.

Another object is to provide such as process which permits the production of high yields of biaryl compounds from difficultly-coupled arylamines.

A further object is to provide such a process which avoids the use of costly, hazardous alkyl nitrites.

These and other objects are attained by coupling an arylamine with an aromatic compound in the presence of water, an inorganic nitrite, and an alkanoic acid containing 5-7 carbons.

DETAILED DESCRIPTION

Arylamines utilizable in the practice of the invention can be any arylamines capable of being coupled with aromatic compounds via diazo intermediates. However, the particular utility of the invention resides in the treatment of arylamines which normally lead to poor yields of biaryl compounds when subjected to Gomberg reactions, i.e., arylamines corresponding to the formula:

$$ArNH_2R_mR'_n$$

wherein Ar is an aryl ring; R is one or more cyanoalkyl, carboxyalkyl, or alkylcarboxyalkyl groups; R' is one or more innocuous substituents, such as alkyl, alkoxy, alkoxycarbonyl, cycloalkyl, phenyl, phenoxy, nitro, halo, cyano, etc.; m is an integer of at least one; and n is 0 or an integer of at least one.

A preferred embodiment of the invention is its application to the coupling of aminohalobenzenes having at least one amino group, at least one halo (i.e., bromo, chloro, iodo, or fluoro) substituent, and at least one of the aforementioned R substituents on a benzene ring—especially one of those aminohalobenzenes in which R is a group corresponding to the formula:

wherein R" is hydrogen or an alkyl group, generally an alkyl group of 1-6 carbons, and Y is —CN or —COOR$_1$ — R$_1$ being alkyl, generally an alkyl group of 1-6 carbons. Exemplary of such compounds are aminohalobenzeneacetonitriles, such as 2-aminofluorobenzene)propionitriles, and alkyl aminohalobenzeneacetic acid esters, such as alkyl 2-(aminofluorobenzene)propionates. Particularly preferred aminohalobenzenes are 2-(4-amino-3-fluorobenzene)propionitrile and alkyl 2-(4-amino-3-fluorobenzene)propionates, which are ideally suited for the preparation of flurbiprofen intermediates by the process of the invention.

Aromatic compounds which can be coupled with arylamines in the process of the invention are substituted and unsubstituted carbocyclic and heterocyclic compounds such as benzene, naphthalene, pyridine, thiophene, etc.—any substituents generally being substituents such as hydroxy, halo, nitro, alkyl, alkoxy, alkoxycarbonyl, aryloxycarbonyl, phenyl, cyano, or cycloalkyl, and any organic substituents generally containing not more than about 10, preferably not more than 4, carbons. The preferred aromatic compounds are benzene compounds, most preferably benzene itself. Since this component of the reaction mixture functions as a solvent as well as a reactant, and the amount used affects the yield of product, it is employed in excess of the amount required to couple with the arylamine. Generally, the amount of aromatic compound employed is in the range of about 50–300, preferably about 100–200, mols per mol of arylamine. Lesser amounts have been found to decrease the amount of biaryl compound obtainable in the process, and greater amounts are somewhat uneconomical.

As indicated above, the process of the invention is conducted in the presence of water; and it has been found necessary to use about 5-15 molar proportions of water per mol of arylamine in order to achieve the production of high yields of biaryl compounds in the process of the invention. The use of either higher or lower amounts of water decreases the yield. Preferably the amount of water employed is in the range of about 10–12 mols per mol of arylamine.

In contrast to the acids employed in the aforementioned prior art processes for conducting Gomberg reactions, the acids employed in the present process are weak acids—specifically, alkanoic acids containing 5–7 carbons. These acids, of course, are pentanoic, hexanoic, and heptanoic acids—the preferred acid being n-hexanoic acid. This ingredient is employed so as to provide about 1–5, preferably about 2–3, molar proportions of acid per molar proportion of the arylamine.

The inorganic nitrite used to diazotize the arylamine may be any of the inorganic nitrites commonly employed in Gomberg reactions, generally sodium or potassium nitrite, and preferably sodium nitrite. The amount of inorganic nitrite employed is preferably such as to provide a nitrite/acid mol ratio in the range of about 1.3–2/1, most preferably about 1.5/1. The use of either a greater or a lesser nitrite/acid mol ratio generally results in a reduced yield of product.

As indicated in the Examples, the reaction conditions—except for those mentioned above—are those conventionally employed in Gomberg reactions. Thus, for example, the reaction is typically conducted at reflux temperatures until a suitable yield is obtained, e.g., for about 20 hours.

If desired, the process may be modified by the use of optional ingredients, such as a cuprous halide, e.g., cuprous chloride, cuprous bromide, etc. When used, the cuprous halide may be initially employed as the halide or a progenitor thereof—most commonly as powdered copper which is reacted with a strong acid, such as trichloroacetic acid, to form the cuprous halide.

The following examples are given to illustrate the invention and are not intended as a limitation thereof.

EXAMPLE I

A mixture of 2 molar proportions of hexanoic acid, one molar proportion of 2-(4-amino-3-fluorobenzene)-propionitrile (AFPN), and 58 molar proportions of benzene was added over a period of two hours to a refluxing mixture of 3 molar proportions of sodium nitrite, 11 molar proportions of water, and 58 molar proportions of benzene. After being refluxed for another 20 hours, the reaction mixture was analyzed and determined to contain a 75.2% yield of 2-(2-fluoro-4-biphenyl)propionitrile (FBPN).

EXAMPLE II

Example I was essentially repeated except that only half as much benzene was employed, and the addition was made at 60° C. instead of at reflux temperature. The analytical yield of FBPN was 65%.

EXAMPLE III

Example I was essentially repeated except that the amount of water was halved and the refluxing was continued for 70 hours. Despite the additional reaction time, the analytical yield of FBPN was only 62.2%.

EXAMPLE IV

Example I was essentially repeated except for employing 3 molar proportions of hexanoic acid, 4 molar proportions of sodium nitrite, and a reflux time of 17 hours. The analytical yield of FBPN was 65.2%.

EXAMPLE V

Example I was essentially repeated except that the hexanoic acid was replaced with an equimolar amount of pentanoic acid, and the reaction mixture was refluxed for 18.5 hours. The analytical yield of FBPN was 67.1%.

EXAMPLE VI

Example I was essentially repeated except that the hexanoic acid was replaced with an equimolar amount of heptanoic acid, and the reaction mixture was refluxed for 18 hours. The analytical yield of FBPN was 69.8%.

It is obvious that many variations may be made in the products and processes set forth above without departing from the spirit and scope of this invention.

I claim:

1. A process which comprises coupling (A) an aminohalobenzene bearing a substituent corresponding to the formula —CHYR″ wherein R″ is hydrogen or an alkyl group of 1–6 carbons, Y is —CN or —COOR$_1$, and R$_1$ is an alkyl group of 1–6 carbons with (B) a benzene compound selected from benzene and hydroxy, halo, nitro, alkyl, alkoxy, alkoxycarbonyl, aryloxycarbonyl, phenyl, cyano, and cycloalkyl substituted benzenes wherein the substituents contain not more than about 10 carbons in the presence of water, an inorganic nitrite, and an alkanoic acid containing 5–7 carbons.

2. The process of claim 1 wherein the aminohalobenzene is an aminohalobenzeneacetonitrile.

3. The process of claim 2 wherein the aminohalobenzeneacetonitrile is 2-(4-amino-3-fluorobenzene)propionitrile.

4. The process of claim 1 wherein the benzene compound is benzene.

5. The process of claim 1 wherein the inorganic nitrite is sodium nitrite.

6. The process of claim 1 wherein the alkanoic acid is hexanoic acid.

7. The process of claim 1 wherein one molar proportion of the aminohalobenzene is reacted with at least about 50 molar proportions of the benzene compound in the presence of about 5–15 molar proportions of water, about 1–5 molar proportions of the alkanoic acid, and an amount of inorganic nitrite such as to provide a nitrite/acid mol ratio in the range of about 1.3–2/1.

8. The process of claim 7 wherein one molar proportion of the aminohalobenzene is reacted with about 100–200 molar proportions of the benzene compound in the presence of about 10–12 molar proportions of water, about 2–3 molar proportions of the alkanoic acid, and an amount of inorganic nitrite such as to provide a nitrite/acid mol ratio of about 1.5/1.

9. A process which comprises coupling 2-(4-amino-3-fluorobenzene)propionitrile with benzene in the presence of water, sodium nitrite, and an alkanoic acid containing 5–7 carbons.

10. The process of claim 9 wherein one molar proportion of 2-(4-amino-3-fluorobenzene)propionitrile is reacted with at least about 50 molar proportions of benzene in the presence of about 5–15 molar proportions of water, about 1–5 molar proportions of the alkanoic acid, and an amount of sodium nitrite such as to provide a nitrite/acid mol ratio in the range of about 1.3–2/1.

11. The process of claim 10 wherein one molar proportion of 2-(4-amino-3-fluorobenzene)propionitrile is reacted with about 100–200 molar proportions of benzene in the presence of about 10–12 molar proportions of water, about 2–3 molar proportions of the alkanoic acid, and an amount of sodium nitrite such as to provide a nitrite/acid mol ratio of about 1.5/1.

12. A process which comprises coupling 2-(4-amino-3-fluorobenzene)propionitrile with benzene in the presence of water, sodium nitrite, and hexanoic acid.

13. The process of claim 12 wherein one molar proportion of 2-(4-amino-3-fluorobenzene)propionitrile is reacted with at least about 50 molar proportions of benzene in the presence of about 5–15 molar proportions of water, about 1–5 molar proportions of hexanoic acid, and an amount of sodium nitrite such as to provide a nitrite/acid mol ratio in the range of about 1.3–2/1.

14. The process of claim 13 wherein one molar proportion of 2-(4-amino-3-fluorobenzene)propionitrile is reacted with about 100–200 molar proportions of benzene in the presence of about 10–12 molar proportions of water, about 2–3 molar proportions of hexanoic acid, and an amount of sodium nitrite such as to provide a nitrite/acid mol ratio of about 1.5/1.

* * * * *